(12) United States Patent
McKenzie et al.

(10) Patent No.: US 10,266,320 B2
(45) Date of Patent: Apr. 23, 2019

(54) HAIR COLORING KIT AND METHODS OF USE AND DOING BUSINESS

(71) Applicant: Cynthia S. McKenzie, Reno, NV (US)

(72) Inventors: Cynthia S. McKenzie, Reno, NV (US); Matthew T. Fisher, Reno, NV (US)

(73) Assignee: Cynthia S. McKenzie, Reno, NV (US)

( * ) Notice: Subject to any disclaimer, the term of this patent is extended or adjusted under 35 U.S.C. 154(b) by 0 days.

(21) Appl. No.: 15/788,656

(22) Filed: Oct. 19, 2017

(65) Prior Publication Data

US 2018/0103743 A1   Apr. 19, 2018

Related U.S. Application Data

(60) Provisional application No. 62/550,185, filed on Aug. 25, 2017, provisional application No. 62/410,063, filed on Oct. 19, 2016.

(51) Int. Cl.
*B65D 51/28* (2006.01)
*B65D 81/32* (2006.01)
(Continued)

(52) U.S. Cl.
CPC .............. *B65D 51/28* (2013.01); *A45D 19/06* (2013.01); *A45D 40/0068* (2013.01);
(Continued)

(58) Field of Classification Search
CPC ................ A45D 40/24; A45D 40/0068; A45D 2200/25; B65D 21/0209; B65D 21/0233;
(Continued)

(56) References Cited

U.S. PATENT DOCUMENTS

| 662,969 | A | * | 12/1900 | Roth Hg | B65D 5/2028 |
| | | | | | 229/115 |
| 879,488 | A | * | 2/1908 | Pitkin | B65D 5/2047 |
| | | | | | 229/112 |

(Continued)

FOREIGN PATENT DOCUMENTS

| EP | 0839736 | * | 5/1998 | ............. B65D 81/32 |
| FR | 2967143 A1 | * | 5/2012 | ......... B29C 49/4278 |

(Continued)

OTHER PUBLICATIONS

Laney College Cosmetology; Hair color retouch; COSME 214: Haircoloring; Instructor: Ms. Ly.
(Continued)

*Primary Examiner* — Tatiana L Nobrega
(74) *Attorney, Agent, or Firm* — Holland & Hart LLP

(57) ABSTRACT

A hair color retouch kit, components of the kit, and methods of use and doing business. The kit can include one or more mixing containers. In one embodiment, a mixing container provides a colorant compartment for sealingly or separately containing a custom hair coloring formulation and peroxide compartment for sealingly or separately containing peroxide. The mixing container(s) can be used by a professional hair colorist to provide a hair coloring client with custom hair coloring formulation and peroxide that can be mixed and applied by or for the client to hair regrowth that occurs after a hair coloring session with the professional. The kit can provide other components as desired, such as a mixing spatula, an applicator brush, and instructions for example. The kit can be packaged in attractive and efficient packaging, include indicia identifying the source of the kit, and be customized to promote the colorist, salon, or other entity.

11 Claims, 20 Drawing Sheets

(51) Int. Cl.
*A45D 40/24* (2006.01)
*B65D 21/02* (2006.01)
*A45D 40/00* (2006.01)
*A45D 19/06* (2006.01)
*A61K 8/22* (2006.01)
*A61Q 5/06* (2006.01)
*B65D 41/04* (2006.01)
*A61Q 5/10* (2006.01)

(52) U.S. Cl.
CPC ............... *A45D 40/24* (2013.01); *A61K 8/22* (2013.01); *A61Q 5/065* (2013.01); *A61Q 5/10* (2013.01); *B65D 21/0209* (2013.01); *B65D 21/0234* (2013.01); *B65D 41/0435* (2013.01); *B65D 81/32* (2013.01); *A45D 2200/058* (2013.01); *A45D 2200/25* (2013.01); *A61K 2800/87* (2013.01); *A61K 2800/882* (2013.01)

(58) Field of Classification Search
CPC .... B65D 21/0234; B65D 51/18; B65D 51/24; B65D 81/32
USPC ........ 206/806, 501, 514; 220/521, 522, 524, 220/529, 527, 504, 4.27, 259.3, 256.1, 220/254.2, 254.8; 229/115; 215/227, 215/228; 132/314, 315
See application file for complete search history.

(56) References Cited

U.S. PATENT DOCUMENTS

| | | | |
|---|---|---|---|
| 2,044,093 A | 6/1936 | Mills | |
| 3,933,297 A * | 1/1976 | Carlsson | B65D 5/12 229/122.22 |
| 4,006,820 A * | 2/1977 | Smith | B65D 81/3205 206/219 |
| D283,592 S | 4/1986 | Quarrell et al. | |
| 4,667,818 A * | 5/1987 | Evans | B65D 51/28 134/18 |
| 4,734,288 A * | 3/1988 | Engstrom | B65D 81/3453 156/275.7 |
| 4,794,008 A * | 12/1988 | Schmidt | A23G 9/48 219/728 |
| 5,209,565 A * | 5/1993 | Goncalves | B65D 81/3211 141/319 |
| 5,223,245 A * | 6/1993 | Ibrahim | A61K 8/02 206/568 |
| 5,551,454 A * | 9/1996 | Goncalves | A45D 19/00 132/202 |
| D433,327 S | 11/2000 | Lillelund et al. | |
| D436,861 S | 1/2001 | Sagel et al. | |
| 6,440,175 B1 | 8/2002 | Stanley, III | |
| 7,051,879 B2 * | 5/2006 | Ramet | B65D 35/22 206/216 |
| 7,270,233 B2 * | 9/2007 | Kindt | B65D 51/28 206/219 |
| D567,078 S * | 4/2008 | Katsuyama | D9/431 |
| 7,407,055 B2 | 8/2008 | Rodriguez | |
| D591,589 S | 5/2009 | Myers et al. | |
| D592,046 S | 5/2009 | Myers et al. | |
| D597,832 S * | 8/2009 | Bischoff | D9/431 |
| D629,657 S | 12/2010 | Carreno | |
| 7,971,716 B2 * | 7/2011 | Eaton | A45C 13/00 206/373 |
| D680,387 S | 4/2013 | Hopkins et al. | |
| D685,232 S | 7/2013 | Lane | |
| 8,550,240 B2 * | 10/2013 | Marcus | A61J 1/03 206/217 |
| 8,757,421 B2 * | 6/2014 | Yang | B65D 51/246 206/223 |
| D697,400 S | 12/2014 | Bragalone et al. | |
| D758,196 S | 6/2016 | Blake et al. | |
| D763,072 S | 8/2016 | Morgan et al. | |
| D786,088 S | 5/2017 | Wilson et al. | |
| 2003/0228336 A1 * | 12/2003 | Gervasio | A45D 34/00 424/401 |
| 2005/0039272 A1 | 2/2005 | Miczewski et al. | |
| 2007/0000070 A1 * | 1/2007 | Vena | A61K 8/19 8/405 |
| 2007/0169285 A1 | 7/2007 | Narasimhan et al. | |
| 2007/0251025 A1 | 11/2007 | Errey et al. | |
| 2008/0083420 A1 | 4/2008 | Glenn et al. | |
| 2008/0178399 A1 * | 7/2008 | Vena | A61K 8/463 8/407 |
| 2010/0154816 A1 * | 6/2010 | Goddard-Clark | A61K 8/19 132/208 |
| 2011/0049081 A1 * | 3/2011 | Bourguignon | B65D 51/28 215/227 |
| 2012/0279879 A1 * | 11/2012 | Lee | B65D 51/285 206/222 |
| 2012/0312811 A1 * | 12/2012 | Savage | B65D 41/26 220/23.83 |
| 2013/0008808 A1 * | 1/2013 | Lee | B65D 47/243 206/221 |
| 2013/0061863 A1 * | 3/2013 | Grey | B65D 21/0228 132/200 |
| 2014/0082854 A1 | 3/2014 | Landa et al. | |
| 2014/0196221 A1 | 7/2014 | D'Amico | |
| 2015/0259115 A1 * | 9/2015 | Yeh | B65D 51/30 206/204 |

FOREIGN PATENT DOCUMENTS

WO    WO 02/083282    10/2002
WO    WO 2013101390    7/2013

OTHER PUBLICATIONS

Coloring Hair Kit; Hair-Highlighting Kits—Hair Color Reviews.
Smart Beauty (https://www.smartbeautyshop.com/); Hair Highlighting Kit.
Simple Charm Beauty; Revlon Frost and Glow Highlighting Kit; May 10, 2013.
Amazon; Buy Soft N Style 10 Piece Hair Colorist Kit.
(http://www.keepbeautiful.ca/shop-by-brand/ombra.html); Standard Colour Kit and Stand.
International Search Report and Written Opinion of the International Searching Authority for International Application PCT/US17/57457, dated Dec. 27, 2017.
Actors Who do Their Own Makeup and Other Beauty Lessons from Broadway; beauty Blitz http://www.beautyblitz.com/makeup/actors-who-do-their-own-makeup-and-other-lessons-makeup-broadway.
Outrageously georgous hair: Why celebs can have it but we can't.

* cited by examiner

HAIR COLORING KIT AND METHODS OF USE AND DOING BUSINESS

CROSS-REFERENCE TO RELATED APPLICATIONS

This application claims priority through, and incorporates by reference, the applicant's prior provisional patent applications, Ser. No. 62/410,063, entitled "Custom Color Retouch Kit And Method," filed Oct. 19, 2016, and Ser. No. 62/550,185, entitled "Custom Color Retouch Kit and Method," filed Aug. 25, 2017.

COPYRIGHT NOTICE

This specification contains material subject to copyright protection. The copyright owner has no objection to the photocopy reproduction of the specification and patent documents in exactly the form they appear in the Patent and Trademark Office patent file or records, but otherwise reserves all copyrights.

FIELD

The present specification generally relates to the field hair color retouching and more particularly to one or more of a kit, or one or more components of a kit, for hair coloring, and methods of use and doing business to provide hair color retouching or one or more retouching components.

SOME ASPECTS OF THE BACKGROUND

Hair coloring has long been a very large industry for a very long time. Today, it is an enormous industry in the U.S. alone.

For example, a First Research report states that, in 2014, there were 82,000 hair salons in the U.S. alone, in addition to 4,000 barber shops. A 2008 Clairol Survey reported that 75% of women in the U.S. between 18 and 65 years of age color their hair, and that 88% of women feel that their hair has an effect on their confidence. Multi-Sponsor Surveys reported in 2012 that 11% of men aged 50-64 color their hair.

A 2005 P&G Beauty Study done by Dr. Frauke Neuser showed that, of the women who color their hair, 52% do so at home only and 48% do so at a Salon (28% at a salon only and 20% at a salon and at home). In 2015, Modern Salon Media conducted a Process Haircolor Research Study, which found that the number one1 reason all women surveyed—home color consumers and salon clients combined—say they color their hair is to color gray and look younger (46%). For women 35 and older, gray coverage becomes even more important, at 65%. This same study found that 48% of salon color clients say they visit a salon every six weeks or more often for services, and 52% visit less frequently and that the overall average interval between salon visits is 7.5 weeks. This same survey found that most salon professionals (64%) say they recommend a "root cover-up" between color appointments, provided either professionally or by use of off-the-shelf coloring products, but 74% of color clients say they have either never had a root cover-up or are unsure if they have ever had one.

Since human hair generally grows at the rate of ½ inch per month, the enormous number of people who have hair coloring done professionally are experiencing substantial regrowth of uncolored hair between coloring services. For most people, the mismatch regrowth is quite visible in the front hairline and hair part within 2 to 3 weeks after a hair color treatment.

How Hair Coloring Works:

The visible part of the hair that is protruding from the skin is called the shaft. The structure of hair shaft is made up the three layers. The outer layer is called the cuticle and consists of overlapping dead cells (like roof shingles) which protect the inner layers. When the cells lie flat the hair reflects light, and looks shiny. When the cells of the cuticle layer are open, the hair feels rough, dry, and looks dull.

The next layer is called the cortex. This is the layer that contains pigment, called melanin, that gives hair it's color.

The innermost layer is called the medulla. This layer is not involved in the color process.

There are three main compounds present in hair dye: ammonia; hydrogen peroxide, and dye intermediates and couplers. Hair typically has a pH level of 5. Ammonia, which is alkaline, is used to initiate the color process by swelling the hair shaft and opening up the cuticle layer.

Hydrogen peroxide is an acid that causes oxidation. The oxidation decolorizes (lightens) natural melanin pigment in the hair cortex and reacts with the color molecules of the chosen permanent hair color pigment to form dye molecules that cannot be washed out.

Hydrogen peroxide is added to hair dye in different concentrations. These concentrations are measured by how many volumes of oxygen are liberated from the decomposition of the hydrogen peroxide, meaning that 10 volume peroxide will form 10 volumes of oxygen from a single volume developer. The higher the concentration of developer, the more oxidation that will occur in a client's hair.

Hydrogen peroxide thus initiates the color process and creates longer lasting color. The larger the volume of peroxide, however, the greater the amount of sulfur is removed from the hair. Loss of sulfur causes hair to harden and lose weight. This is why for most hair coloring services, the peroxide level is maintained at 30 volume or less.

The dye or coloring intermediates and couplers are small compounds that fit into the opened cuticle of the hair shaft. Once they mix with hydrogen peroxide, they become larger color molecules that cannot depart the hair shaft.

How Professional Permanent Hair Color is Used:

The professional hair colorist begins by examining the clients hair texture, dryness, natural hair color, and amount of gray hair, which is coloring resistant. From those factors the colorist determines the formulation of various pigments (dye) and enhancers to be used to achieve the desired result. Next, the colorist determines the volume of peroxide required according to the various factors. Then the colorist blends the pigment formulation with the peroxide formula. When the mixture is completely blended, it is applied to the client's hair.

The chemical process of pigment (color) becoming permanent in the hair shaft usually requires between 20-30 minutes to complete. The color formulation remains on the clients hair for that period of time in order to fully develop (replace color in the client's hair). After the prescribed period of time for development, the color molecules of the permanent hair color have expanded and are permanently fixed into the hair shaft. The hair is then shampooed, rinsed, and styled.

Because the peroxide component ($H_2O_2$, more fully referred to as "hydrogen peroxide") is an acid, it is typically pre-mixed with water to dilute the peroxide in the resulting peroxide/water mixture. Nevertheless, even with this lower concentration of peroxide, if the resulting hair color formulation of colorant, water, and peroxide makes contact with human skin or hair for too long or with an excessive concentration of peroxide, the peroxide in the formulation can excessively oxidize, excessively dry, and damage the skin or hair or at least leave it with a dull finish or lack of shine. This is one reason why the professional colorist usually applies the colorant formulation with plastic gloves, to protect the colorist's skin from contact with the peroxide component of the formulation. This is also why the professional colorist makes adjustments to the colorant formulation applied to a given client in repeat coloration sessions over time, to ensure that the client's hair remains in a healthy condition. These risks are reasons that hair coloring is so commonly performed by a professional hair colorist.

Another reason is that, as noted above, the colorant component is typically customized by the professional colorist, by mixing one or more color components (usually at least two to three pigments or dyes), often with one or more other enhancers, to yield the color shade desired in the resulting colorant formulation. The professional hair colorist typically has in-depth knowledge of differing brands of hair coloring components and their differing qualities; and this knowledge plays a crucial role in adjusting the shades and strength of colors for differing clients, including by taking into account each client's hair texture, dryness, hair density, and natural color, including the amount of gray hair. After sufficient processing time in the client's hair, which can vary by client, the colorist rinses the client's hair to remove remaining colorant formulation not absorbed the hair. For all these reasons and others, such as convenience and combining the hair coloring process with procuring a haircut, clients seeking hair coloring commonly have the hair coloring formulation prepared and applied by professional hair colorists rather than by the clients on their own.

The Age-Old Problem of Hair Regrowth after Hair Coloring:

Within one to two weeks after hair is colored by professional colorists, clients typically experience visible naturally-colored hair regrowth, particularly around their front hairlines and at any parting lines within their hair. Since most hair color clients do not have the time or money to have their hair color professionally retouched every one to two weeks, their only options are to either maintain the visible regrowth, or to try and match the professional color with a hair coloring product acquired at a store or from an online commercial source.

The latter nonprofessional hair color products are, however, vastly inferior to professional hair coloring. One reasons is because over-the-counter products, designed as one size fits all, typically include an excessive concentration of peroxide—sometimes close to 40 volume in order to ensure maximum coloring of resistant gray hair—as compared to the much lower concentration that would be utilized by professional colorists for most clients.

In addition, since, as noted above, the professional colorist typically mixes different colors and possibly enhancer—often multiple different enhancers as well—to achieve a desired hair color shade for the client's particular type of hair and natural color, the client usually does not have the knowledge or formulation components to achieve anything close to the professional's hair color shade in the client's hair. The results of a non-professional use of off-the-shelf hair coloring products commonly are bands of colors that do not match, do not last and or easily washed out by shampooing, can cause the scalp to itch, and/or do not provide the desired resulting hair color, particularly in grey hair.

With regard to grey hair in particular, many off the shelf retouching products contain little or no peroxide. With little or no peroxide in the hair coloring formulation, grey hair cuticle in particular does not open and therefore does not become colored.

For these and other reasons, it is also common for clients who use home coloring products or kits to at least eventually experience an undesirable result in hair color and hair damage. When this occurs to given client, the client's choices are to either live with the problem until the client's hair grows out, or have the problem corrected by a professional colorist. The corrective process is typically much longer and more expensive that normal professional coloring services, and the process usually yields yet further dryness and hair breakage.

So, while home-hair color products have long been widely available and themselves a substantial part of the huge hair coloring industry, they have long provided results that are inferior to the typically much more aesthetically attractive results of professional hair coloring, including when used to re-touch hair color between professional coloring sessions. At the same time, professional colorists have typically constantly sought additional ways to enhance their product and service offerings and increase resulting profitability as well. This has been the state of the hair coloring industry for well over 40 years.

BRIEF SUMMARY OF SOME ASPECTS OF THE SPECIFICATION

The applicant has developed a hair coloring kit and method of use and doing business. In some embodiments, the kit provides pre-mixed colorant (such as multiple differing hair coloring colors and, optionally, one or more hair coloring enhancers), and optionally peroxide, to or for an individual, with the colorant custom pre-mixed to match or compliment other hair colorant applied to the individual. The individual or other person can then mix the pre-mixed colorant with the optional or other peroxide for application of the resulting colorant formulation to hair on the individual.

In some methods, the pre-mixed colorant is pre-mixed by or for a professional hair colorist, and some methods include the pre-mixed colorant being provided by or for the professional hair colorist to or for a client of the professional hair colorist. Some methods include generation of the pre-mixed colorant during or in connection with a hair coloring session for the client. In some instances, the pre-mixed colorant is a portion of colorant also generated and applied to the client during a professional hair coloring session.

The kit and method can further be used to solve the age-old problem of maintaining the color of hair, such as regrowth for example, after a hair coloring session, such as a professional hair coloring session for example. Consequently, some instances can include the kit being used by or for the client to color the client's hair after the hair coloring session, which may take place, in some embodiments, up to weeks, months, or more after the hair coloring session.

The kit can include, in addition to pre-mixed colorant and/or peroxide, a mixing container, a mixing tool, an applicator brush, instructions for use, one or more other possible components such as a mirror, which may be lighted, and packaging for the kit. The packaging or one or more other components may have indicia of varying types, and in some embodiments some or all the indicia may be customized for the hair colorist professional, a salon, or provider of the kit. In some kits, the packaging or other one or more other components can include outer trademark indicia and may also include indicia otherwise customized, such as by printing or marking on the actual packaging or by label(s) applied to the packaging.

Packaging for some kits can have an attractive shape, such as a triangular outer shape for example. Some instances can provide a relatively small, lightweight, or easily displayed package.

One particular type of packaging can be have a plurality of triangular sides and be small, lightweight, and easily displayed on either a shelf or by being hung on a mounting rod or other mounting element. The packaging may include a mounting rod channel passing through the packaging—for example, through a narrower end of the packaging as compared to an opposed thicker end.

Some kits may include a single container providing separate chambers or compartments for storage of colorant separately from other material such as peroxide for example. The colorant may then be mixed with the other material by opening the container, removing one or more sealing structures, and mixing the colorant with the other material.

Some instances of the container can include a first portion and a second portion, and the first portion and second portion may be removably mountable to each other such as by mating threads for example. The first portion may have a first removable seal, such as on the one outer side of the first portion, and may have a second or other seal mountable spaced from the upper removable seal. The second portion may include a second section sealing element as well.

The packaging and container may be sized so that separate container compartments can be secured within the container so that, when the packaging is opened, the separate compartments can be filled with differing hair coloring materials, removed from the packaging and mounted together to provide the container and mixing of the differing hair coloring materials within the container, and then remounted within the packaging along with any other kit components. In some embodiments, the packaging may have a plurality of triangular sides providing a relatively thickened end opposite a pointed end, and the mixing container can be mounted in the thickened end of the packaging for delivery to or for a hair coloring client.

Some methods of mixing container use may include placing hair colorant in the first or second portion of the container and peroxide or other material in the other portion of the container. Some such methods may include then inserting second or other removable seal in the first portion of the container and the second section removable seal in the second portion of the container. The first and second portions may then be mounted to provide a container containing the colorant and peroxide or other material, with at least one removable seal separating the colorant from the peroxide or other material within the container.

The colorant and peroxide or other material may then be mixed by separating the first section of the container from the second section, removing at least one or more removable seal, remounting the first and second sections to provide a container and mixing of the colorant, peroxide, or other material within the container.

Some embodiments of the container provide the first section of the container having both the first removable seal and second removable seal spaced from the first removable seal and optionally a second section removable seal within the second section. The differing components are placed in the differing container sections so that they are maintained separately from each other by the removable seals. The components may then be mixed by separating the container sections, removing one or more seals, remounting the container sections, removing an outer seal to provide an open side, such as an upper side for example, in the container and mixing the components such as with a mixing tool penetrating the open side.

In some embodiments, one or more of the hair colorant or other coloring process material may be in a gel within the container. The gel may be sufficiently thick and self-adhering that the gel remains in place within the container even after associated sealing structure is removed. In some such embodiments, the container section containing the gel can therefore be separated from another container section to remove the associated sealing structure and then remount gel containing section over the other container section without the gel spilling out of the gel containing section. Some instances can include an upper removable seal that is then removable in order to mix the components within the container such as with a mixing tool.

In some embodiments, the mixed coloring components in the container can thus provide colorant that can be applied to hair. The hair may be that of professional colorist client in order to maintain the desired color on the client after receiving professional hair coloring by or for the professional colorist.

Some instances of the method can thus provide a promotional or revenue source, such as for a salon, a professional hair treatment center or colorist, or other business or activity. The kit can be sold for example. It may also provide a marketing or promotion vehicle through inclusion of indicia on one or more of the kit packaging and components.

It is to be understood that, while the foregoing discussion has been dominantly in the context of human hair coloring, the hair involved may be animal or plant hair or any other regrowth of any type. Further, the kit components may be mixed and matched as desired and may be used in applications and with components other than those identified in this Summary section.

It is also to be understood that there are other novel aspects of this specification. They will become apparent as this specification proceeds. In this regard, the scope of the invention is to be determined by the claims as issued and not by reason of whether a given feature or feature set is included in this Brief Summary or addresses an issue in the Background section of this specification.

BRIEF DESCRIPTION OF THE DRAWINGS

The applicant's preferred and other embodiments are shown in the accompanying drawings in which.

DETAILED DESCRIPTION

The following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

Figure 1:
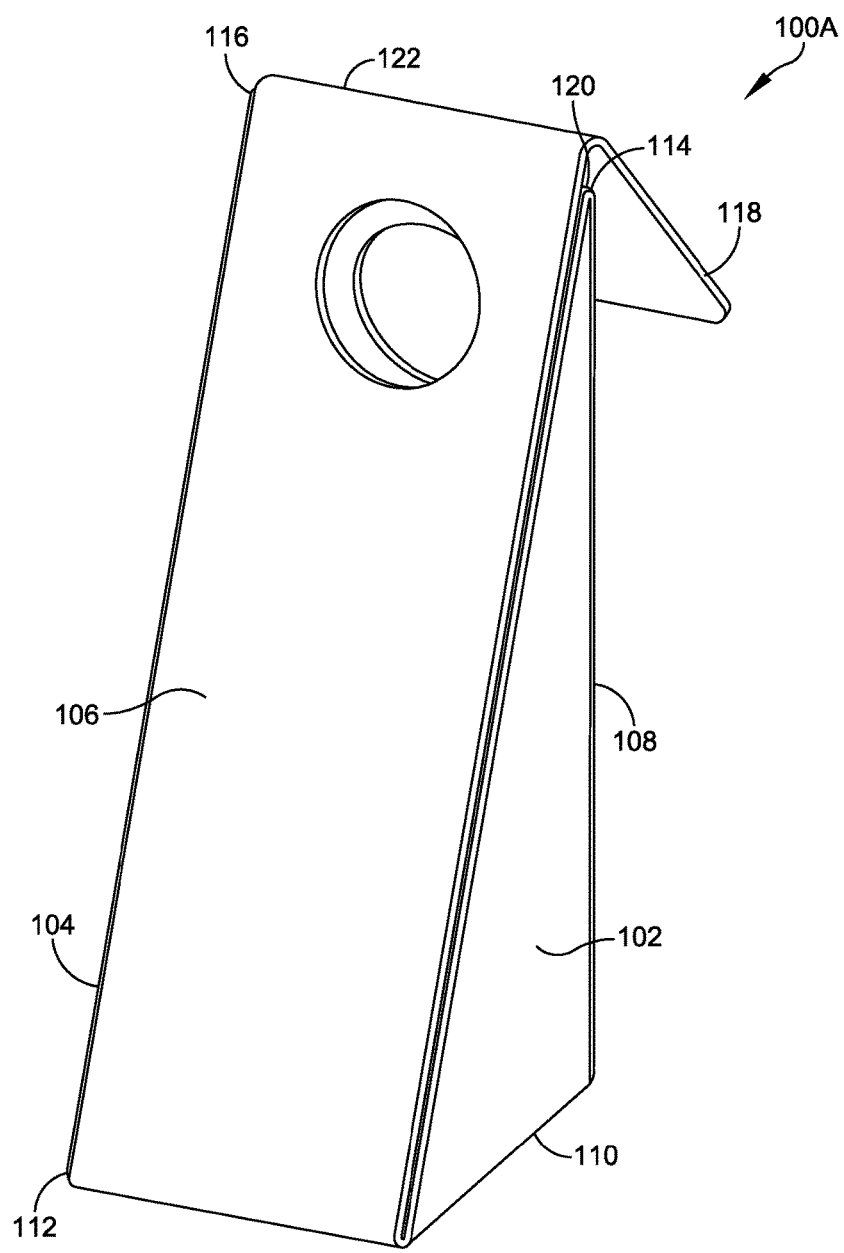
FIG. 1 is a perspective view of a hair coloring kit of this specification.

With reference now to FIG. 1, one embodiment of a hair retouching kit package, generally 100A, has two opposed, parallel, planar triangular sides 102, 104 spaced apart from each other by two mostly opposed and mostly planar rectangular sides 106, 108. Each rectangular side, e.g., 106 extends from the widened ends 110, 112, of the opposed triangular sides 102, 104, respectively, to the narrower pointed ends 114, 116, of the opposed triangular sides 102, 104, respectively. One rectangular side 106, however, also has an extended folding end 118 that can fold around the opposed rectangular side end 120 spanning between the opposed narrower pointed ends 114, 116 of the opposed triangular sides 102, 104. A circular mounting pole passage 122 extends through the opposed rectangular sides 102, 104 and through the extended folding end 118 spaced from, but relatively close to, the folding end 124 of the extended folding end 118.

Figure 2:
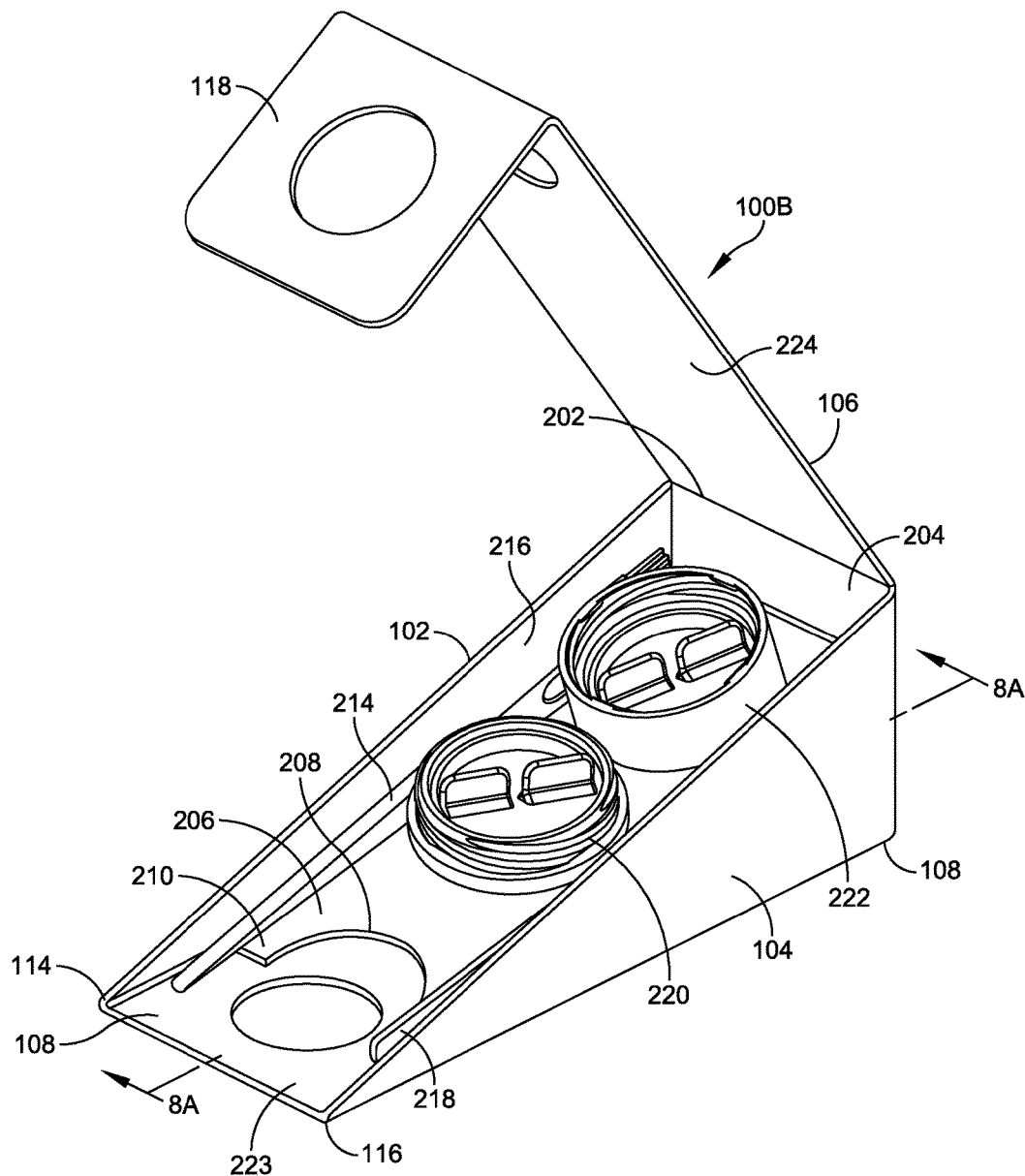
FIG. 2 is a perspective view of another hair coloring kit of this specification opened and showing contents of the kit and having a right angled corner in opposed triangular sides of the package.

With reference now to FIG. 2, the kit package 100B can be opened by unfolding the extended folded end 118 and lifting that end 118 to cause the extended rectangular side 106 to rotate away from the pointed ends 114, 116 of the opposed triangular sides 102, 104 about the edge junction 202 of the widened package end 204 opposite the pointed ends 114, 116. A removable kit component mounting platform insert 206 extends from the widened end 204, spaced from the shorter rectangular side 108 opposite the extended rectangular side 106, toward the opposed pointed ends 114, 116 of the opposed triangular sides 102, 104 to terminate in a semi-circular cutout end 208 with opposed arms 210, 212 (212 not shown) abutting the shorter rectangular side 108 spaced from the opposed pointed ends 114, 116 of the opposed triangular sides 102, 104.

With reference now to FIG. 2, in another particular embodiment of the kit package 100BB: the triangle sides, e.g., 104, each have outer peripheral triangle dimensions of 3×8.25×8.75 inches. The widened end 204 is a 3×3 inch square. The rectangular lower side 108 has outer peripheral dimensions of 3×8.25 inches. These dimensions can be varied by plus or minus 60%. The package 100B and its removable mounting platform insert 206 can each be made from a single folded piece of paper, cardboard, plastic sheet, or other suitable material.

Multiple kit packages, e.g., 100B, are thus readily stackable and packaged, such as by inverting one package with respect to another and rotating it 180 degrees in a vertical plane and stacking the inverted package on top of a base non-inverted package to yield a rectangular box-like structure provided by the stacked two packages. This same stacking technique can be repeated as many times as desired, including if desired by placing stacked packages side-by-side, to yield and overall rectangular structure of packages, e.g., 100B, without any wasted or unused space in the stacked package structure.

The kit package 100B contains an applicator brush 214 abutting the interior side 216 of one triangular side wall 104, a mixing spatula 218 abutting the opposing interior side (not shown) of the opposite triangular side wall 102, a mixing container top compartment 220 mounted inverted in this location, and the bottom compartment 222 mounted upright intermediate the applicator brush 214 and mixing spatula 218. The kit package may include kit use instructions (not shown), and they may be folded and contained under the component mounting platform insert 206 or printed on the interior side 224 of the extended folded end 118.

Figure 3:
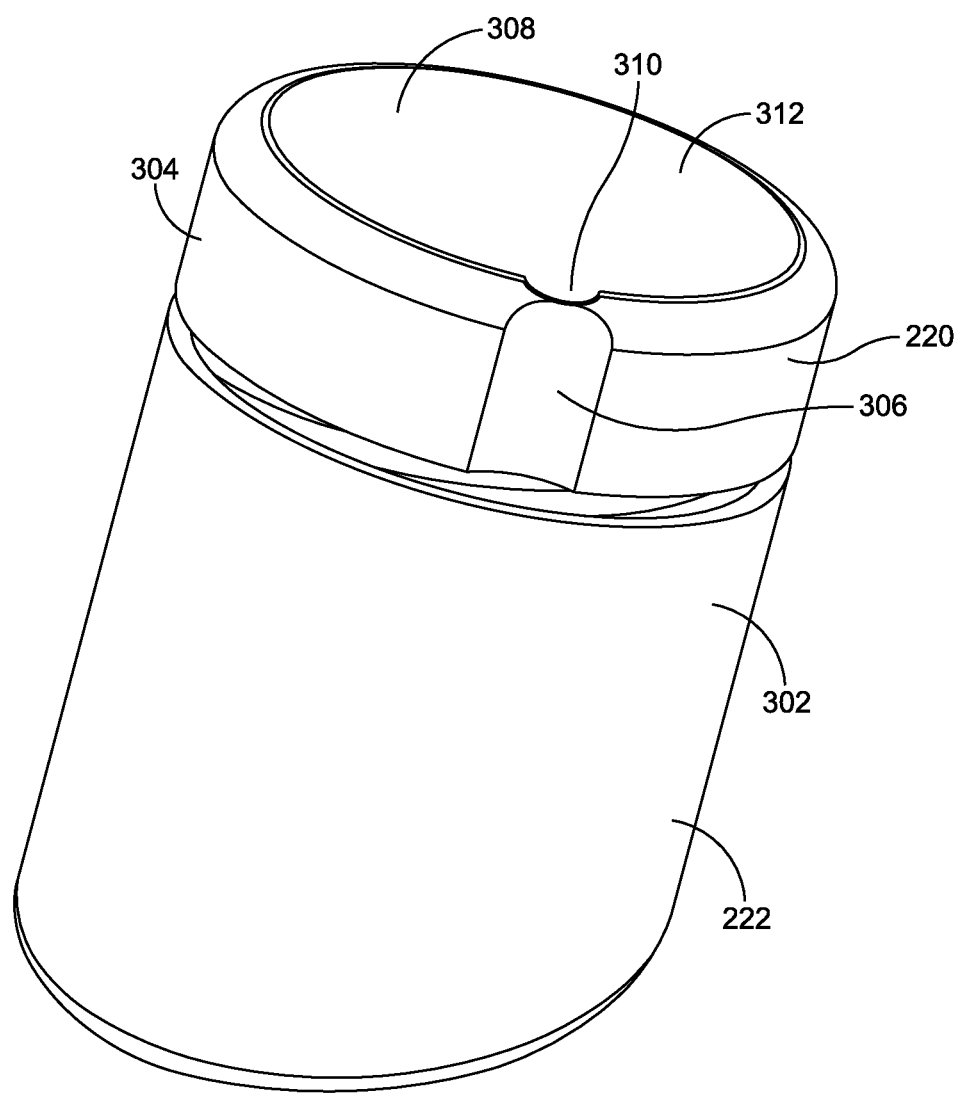
FIG. 3 is perspective view of hair coloring mixing container of the kit of FIG. 2.

With reference now to FIG. 3, the assembled mixing container 302 has the generally tubular top compartment 220 removably threaded to the relatively larger, generally tubular bottom compartment 222. The outer circumferential periphery 304 of the top compartment 220 has an finger placement indent 306 penetrating radially inwardly through the circumferential periphery 304. The planar top side 308 of the top compartment 220 consists a removable, generally circular, removable planar seal 308 spanning across a tubular channel (not shown in FIG. 3) in top compartment 220 underlying the circular planar seal 308. The planar seal 308 has a grippable lip 310 extending radially outwardly from the central circular body 312 of the circular planar seal 308.

Figure 4:
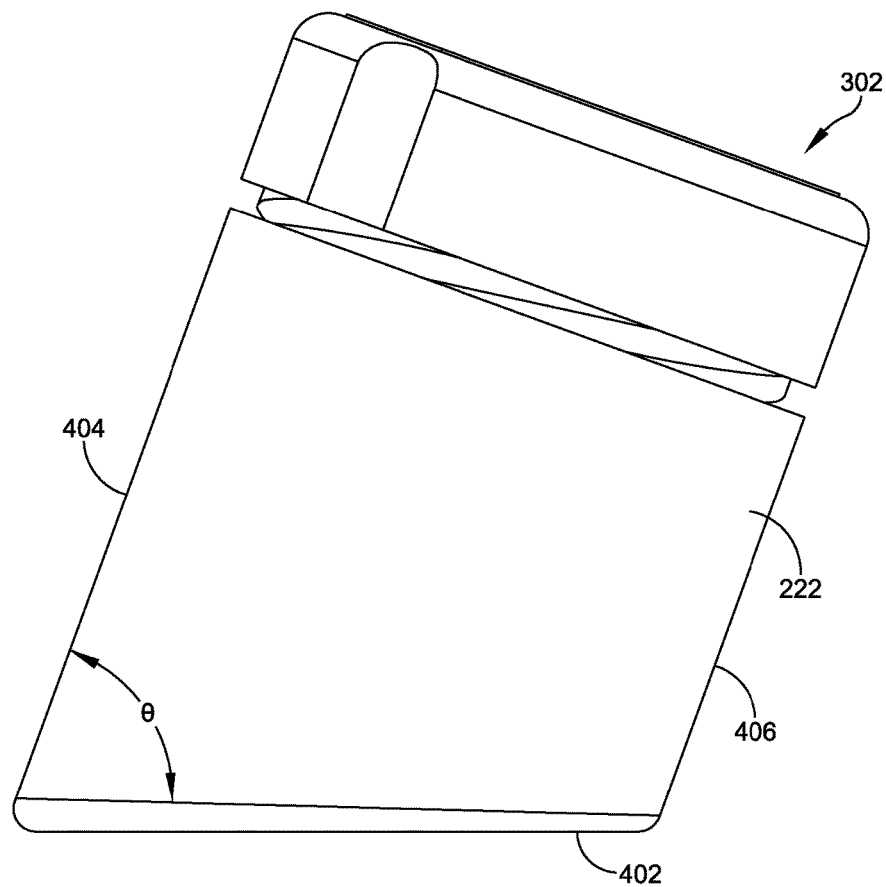
FIG. 4 is a right side elevational view of the hair coloring mixing container of FIG. 3.

With reference now to FIG. 4, the bottom compartment 222 has a planar bottom end 402 extending at an acute angle from the longer laterally extending side 404 of the bottom compartment 222 to the other, shorter laterally extending side 406 of the bottom compartment 222, in the depicted embodiment, that angle Θ is 73 degrees, bit this angle can be varied, such as up to plus 5 more degrees or less 25 degrees as but one example, to accommodate differently sized components or even those identified in detail in this specification. 73 degrees allows, as shown in FIG. 2, a larger volume bottom compartment 222 to be mounted in the kit package 100B with the planar bottom end (not shown in FIG. 2) parallel to, and matingly abutting, the adjacent portion (not shown in FIG. 2) of the planar interior side 223 of the shorter rectangular side 108 of the kit package 100B.

Figure 5:
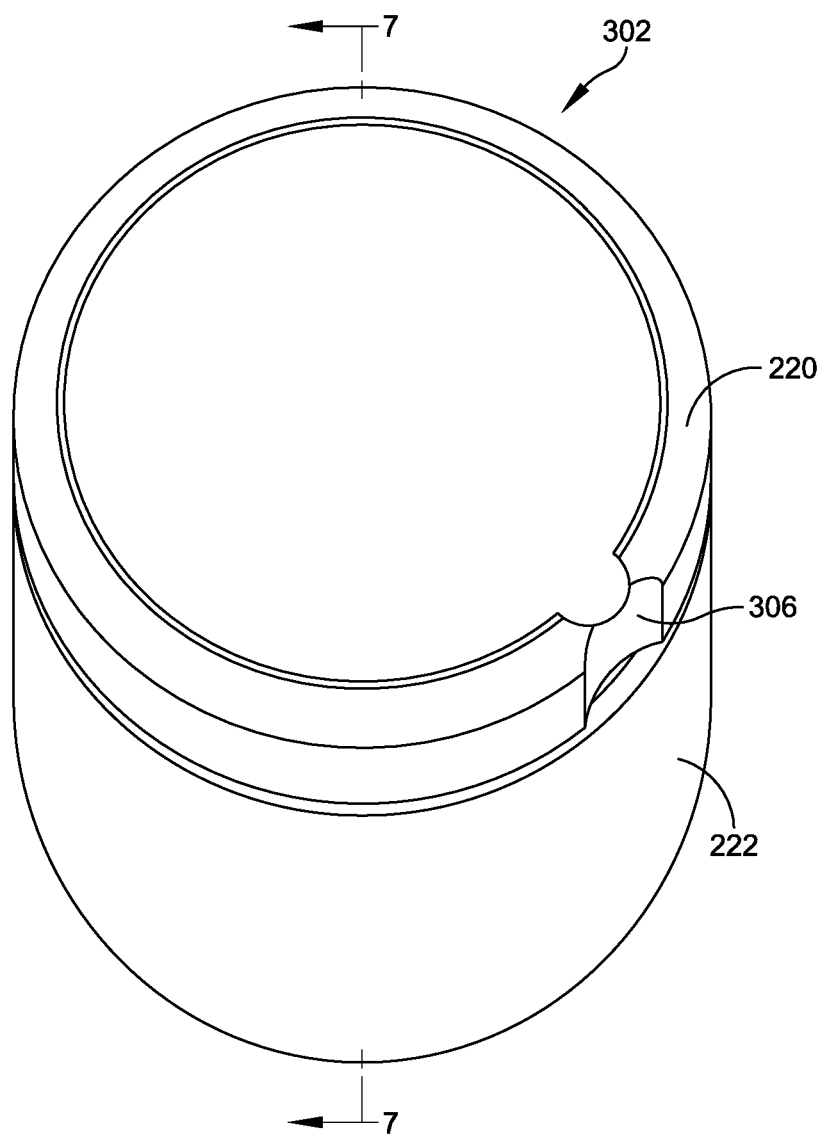
FIG. 5 is a top plan view of the hair coloring container of FIG. 3.

With reference now to FIG. 5, this top plan view shows how the assembled mixing container 302 also inherently tilts with respect a planar horizontal surface (not shown in FIG. 7), such as a table, on which the assembled mixing container rests. In this position, a person can grasp the top compartment 220 with one hand (not shown) and the bottom compartment 222 with another hand (not shown), while the thumb of the one hand penetrates the finger placement indent 306 in order to rotate the top compartment with respect to the bottom compartment.

Figure 6:
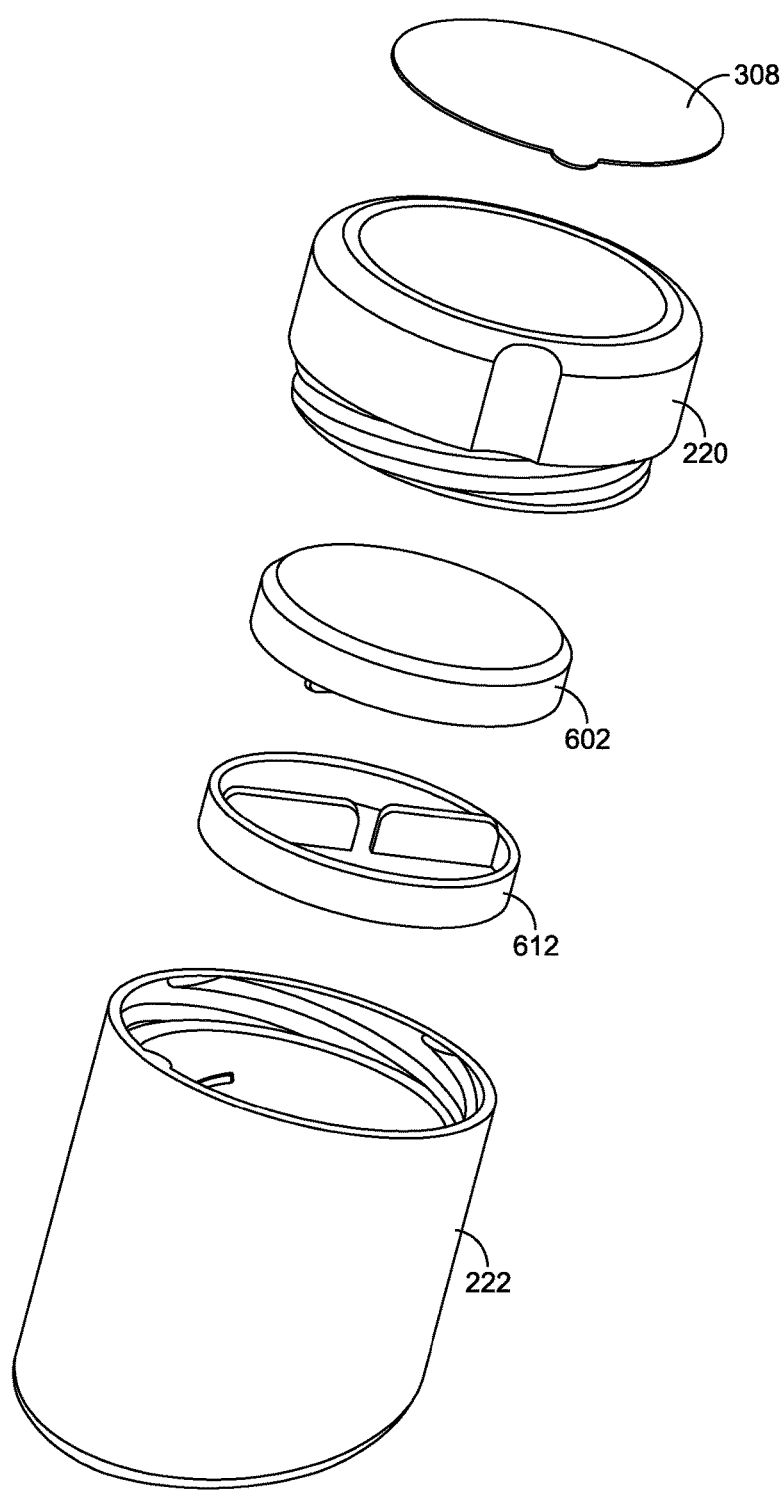
FIG. 6 is an exploded perspective view of the mixing container of FIG. 3.

Referring now to FIG. 6, the components of the mixing container 302 include not only the top compartment 220, its removable top planar seal 308, and the bottom compartment 222, but also a resilient, removable, and replaceable top compartment interior seal 602, and an identically structured but inverted (as compared to the top compartment interior seal 602) bottom compartment interior seal 612. The top compartment interior seal 602 is slidably mounted within the top compartment 220, and the bottom compartment interior seal 612 is slidably mounted within the bottom compartment 222. The components of the mixing container 302 may be made from materials as follows:
- the top section 220 and bottom section 222 may be made of any suitable strong plastic (such as nylon, acrylic, PVC, polyethylene, polypropylene, polycarbonate, bakelite, melamine, etc.), glass, composite, or metal;
- the interior seals 602 and 612 may be made of resilient material such as plastic for example; exemplary plastics can include polyethylene, polypropylene, polyurethane, etc; and
- the top seal 308 may be made of resilient material such as plastic (such as identified above), Teflon sheet, foil-lined paper, PET, aluminum sheet; and it 308 may be adhered in position on the top edge of the top section 220 by any suitable adhesive.

Figure 7:
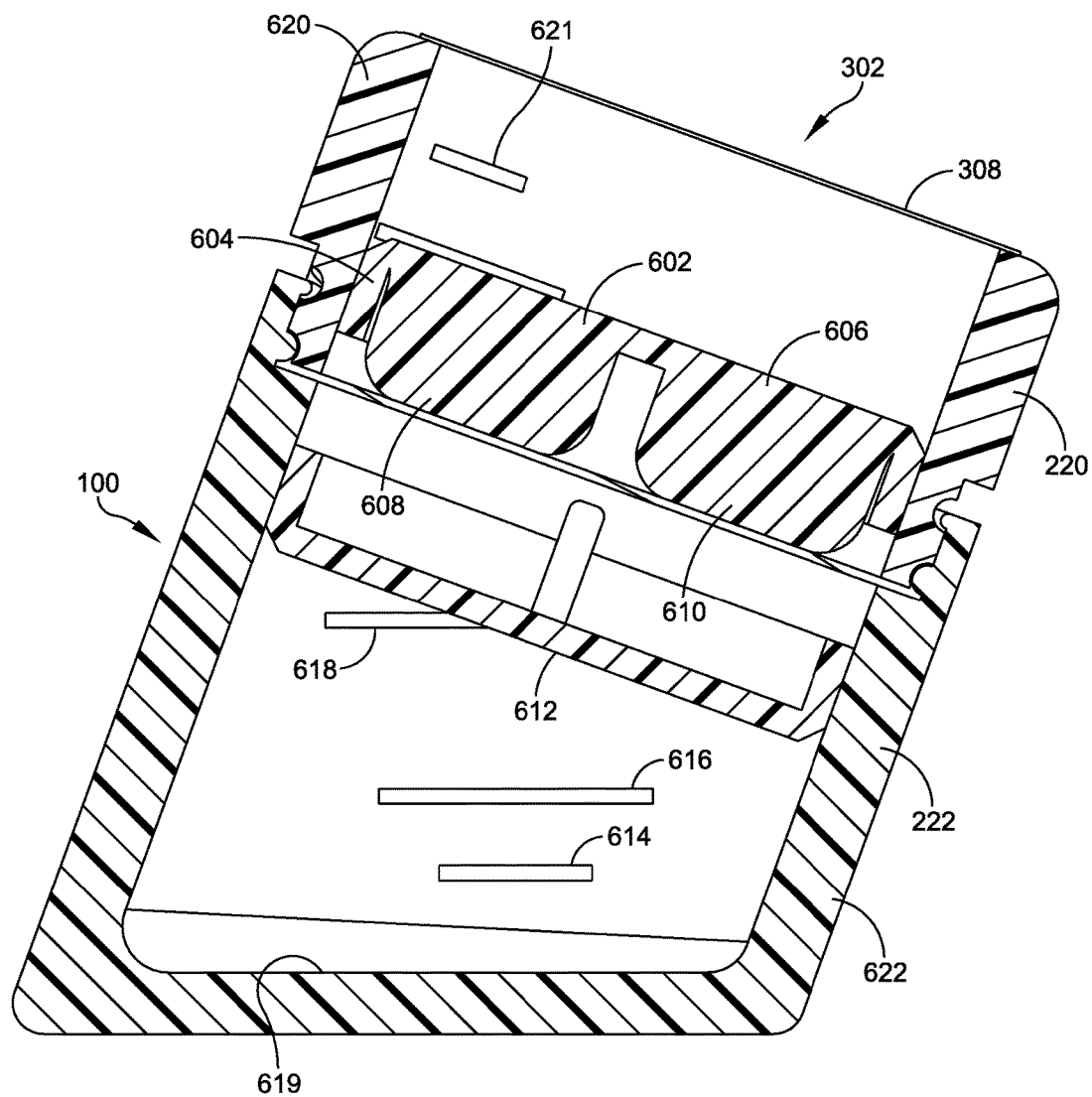
FIG. 7 is a cross-sectional view taken along section line 7-7 of FIG. 5.

Referring now to FIG. 7, the mixing container 302 as delivered to a user, such as professional hair colorist for example, may be assembled as shown in FIG. 4 rather than in the separated format of FIG. 2. In either event, as provided for use by a professional colorist to provide a coloring kit to a client, the top interior seal 602 has (i) a tubular side sealing wall 604 extending from a planar sealing end 606 and (ii) opposed grippable tabs 608, 610 (a) extending downwardly from the planar sealing end 606 in the orientation of the seal 602 shown in FIG. 2 and (b) surrounded by the tubular side sealing wall 604. The opposed tabs 608, 610 are spaced from each other about the axis of the top compartment 220.

In addition, the bottom compartment seal 612 is spun about its axis, such as by 20 to 90 degrees, to the orientation of the top compartment inner seal 602. The spacing apart of the opposed tabs, e.g., 608, 610, allows the opposed interior seals 602, 612 to come closer together within the mixing container 302 if desired without the opposed tabs from the opposed seals 602, 612 bumping into each other in blocking fashion.

Each compartment has internal sidewall linear markings, e.g., 614, 616, 618. These markings provide fill level indicia to the user when the user places fluid or gel within each of the respective top and bottom compartments 220, 220 as explained further infra. The linear markings 614, 616, 618 of the bottom compartment 222 are parallel to the generally planar bottom surface 619 in the bottom end 402 of the bottom compartment 222. This allows the markings, e.g., 614, 616, 618, to be horizontal as the bottom compartment is filled with fluid as explained infra.

In contrast, the linear level markings, e.g., 621, of the upper compartment are parallel to planar upper seal 308 in the top compartment 220. This allows these markings, e.g., 621, to be horizontal as the top compartment 220 is inverted and filled with material as also explained further infra.

Figure 8A:
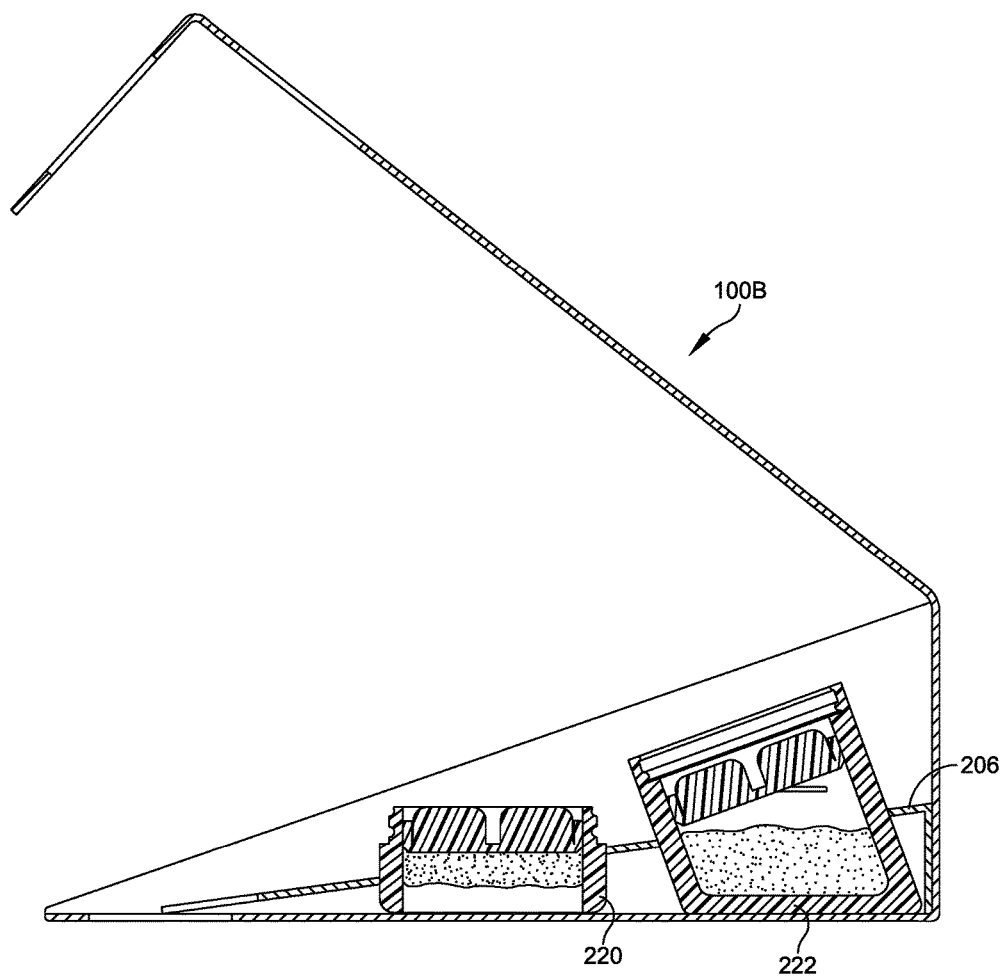
FIG. 8A is a cross-sectional view taken along section line 8A-8A of FIG. 2.
Figure 8B:
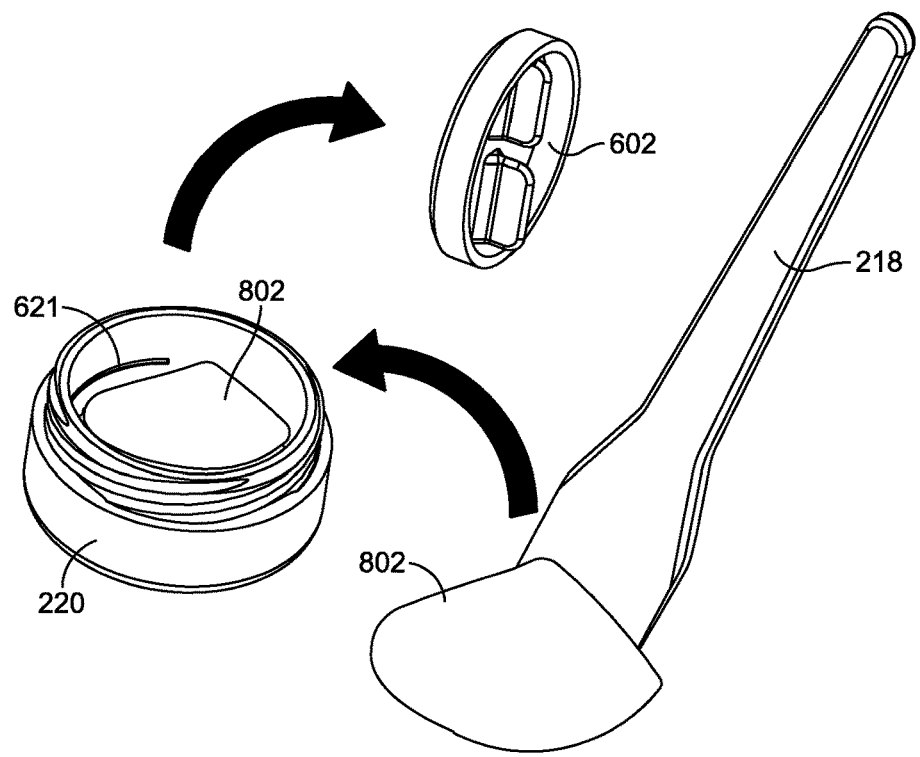
FIG. 8B is a perspective view of the container top section of FIG. 9A and mixing spatula and hair coloring gel during insertion of the gel into the top section.
Figure 8C:
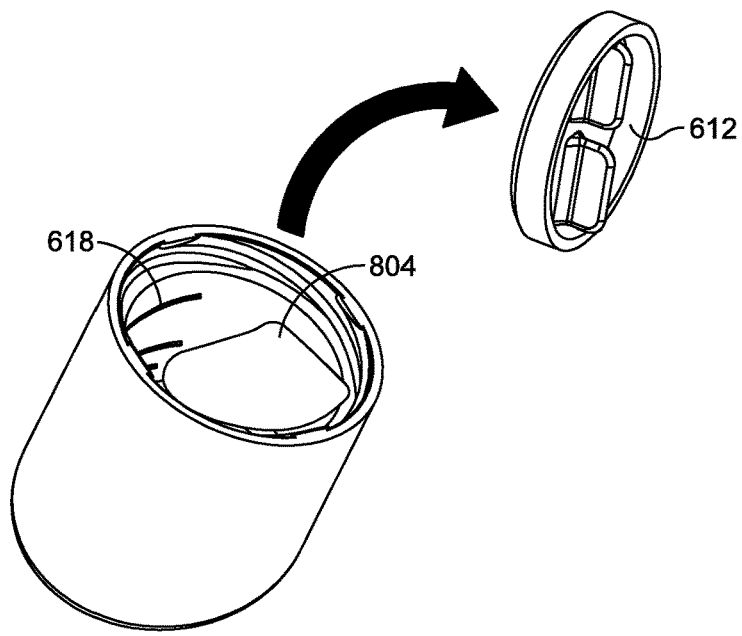
FIG. 8C is a perspective view of the container bottom section of FIG. 9A with peroxide poured into the bottom compartment.
Figure 8D:
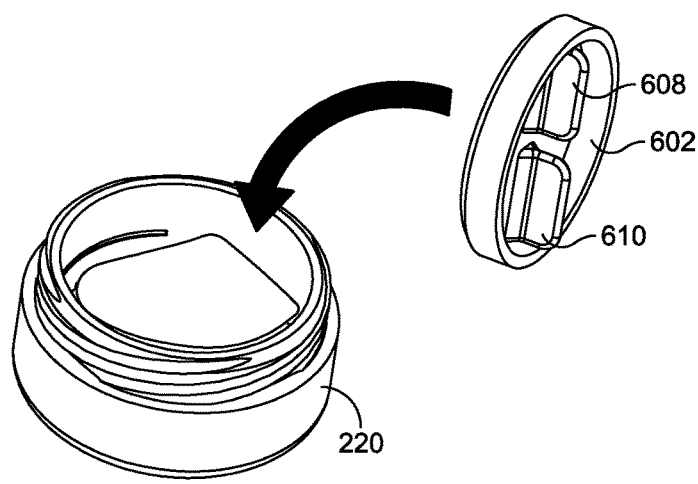
FIG. 8D is a perspective view of the container top section of FIG. 8A and a removable top section resilient seal prior to insertion into the interior of the container.
Figure 8E:
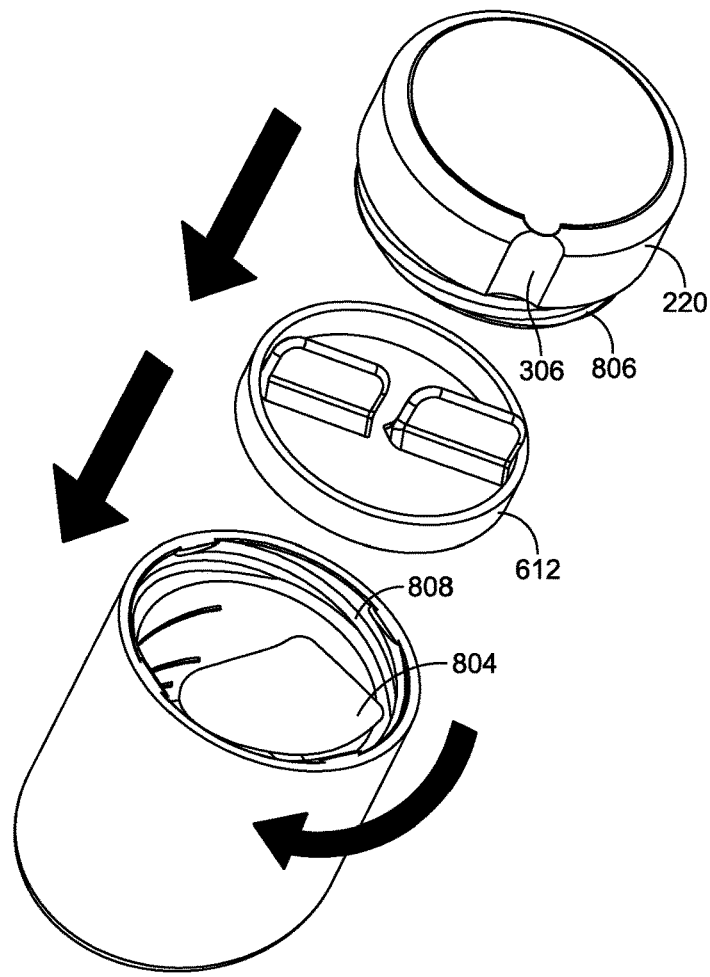
FIG. 8E is a perspective view of the container bottom section of FIG. 9A and a removable bottom compartment resilient seal prior to insertion into the interior of the container bottom compartment.
Figure 8F:
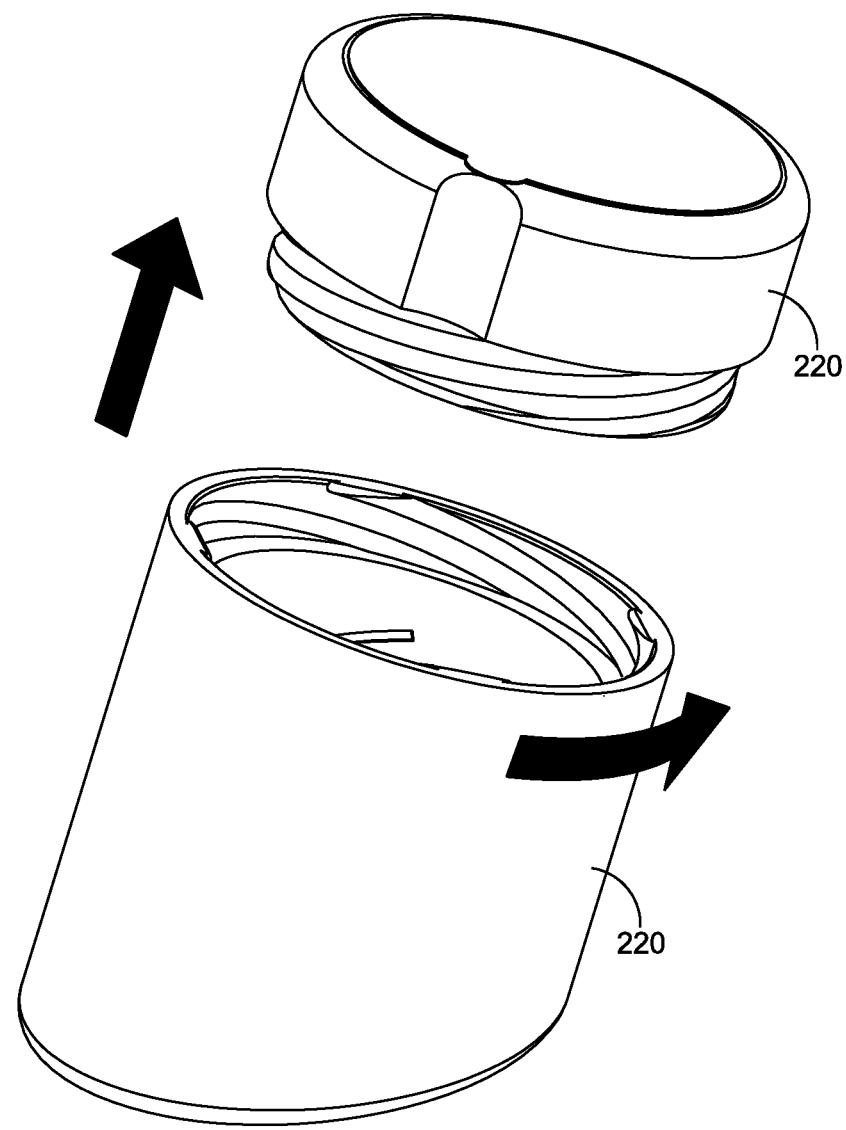
FIG. 8F is a perspective view of the container top section being mounted to the bottom section (conversely by reverse rotation with respect to each other, being separated from the bottom section)
Figure 8G:
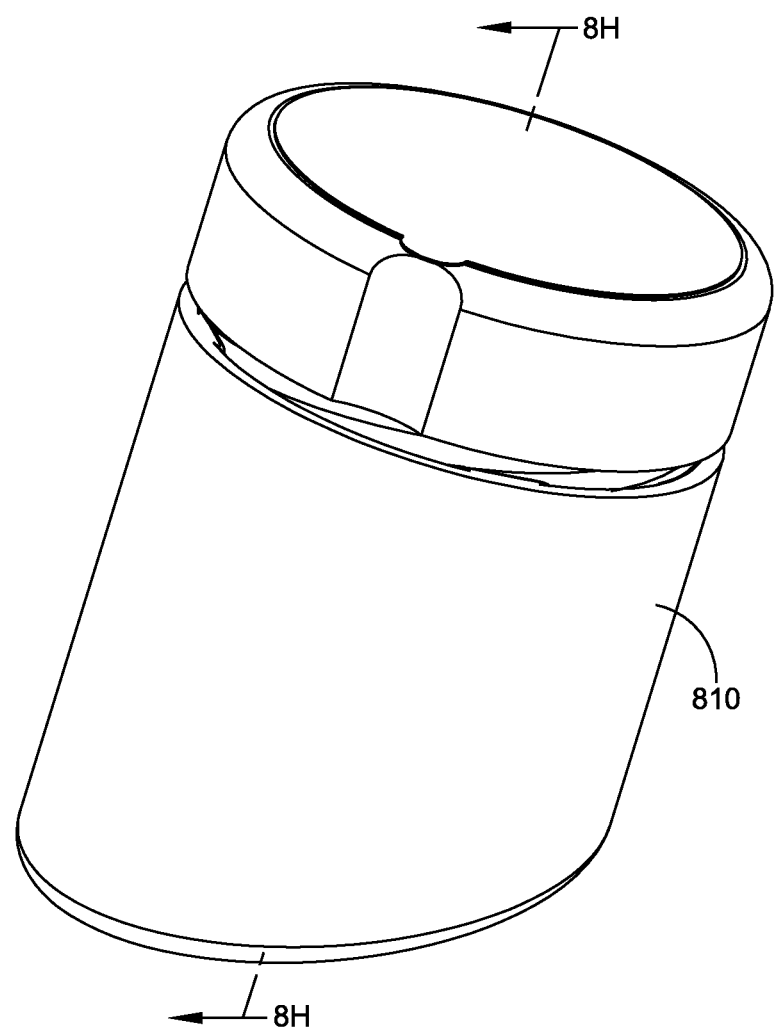
FIG. 8G is a perspective view of the assembled hair coloring container of FIG. 9E.
Figure 8H:
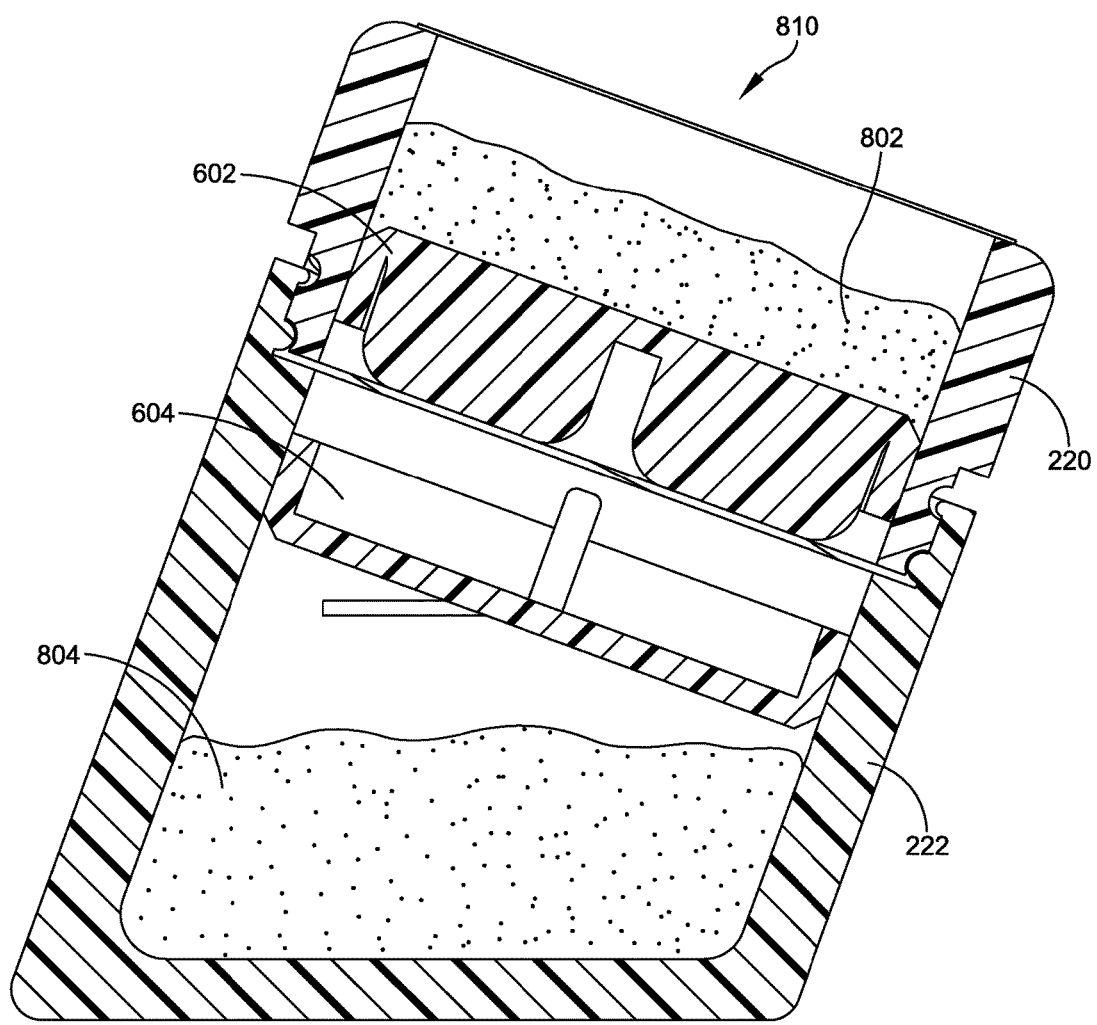
FIG. 8H is cross-sectional view taken along section 8H-8H of FIG. 9G.
Figure 8I:
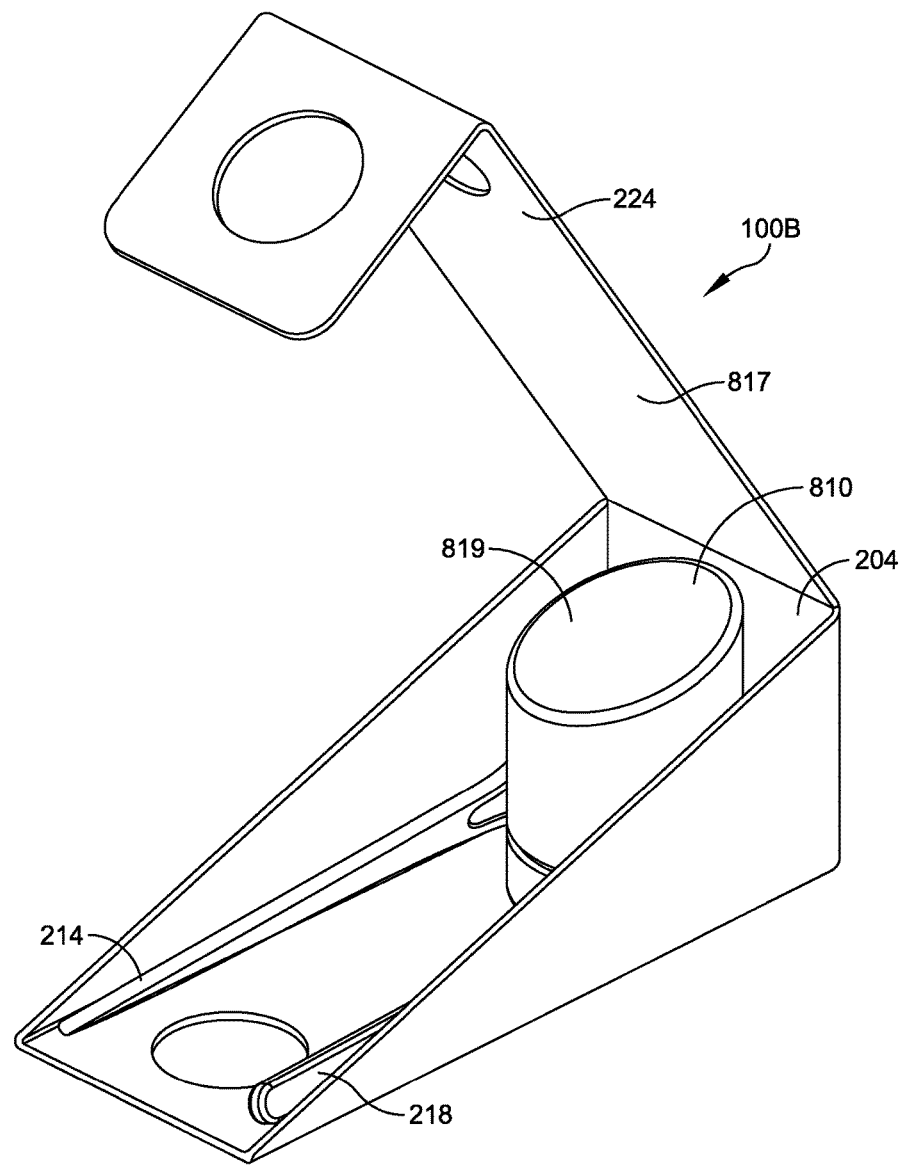
FIG. 8I is perspective view of the assembled hair coloring container placed in the open kit packaging.
Figure 9:
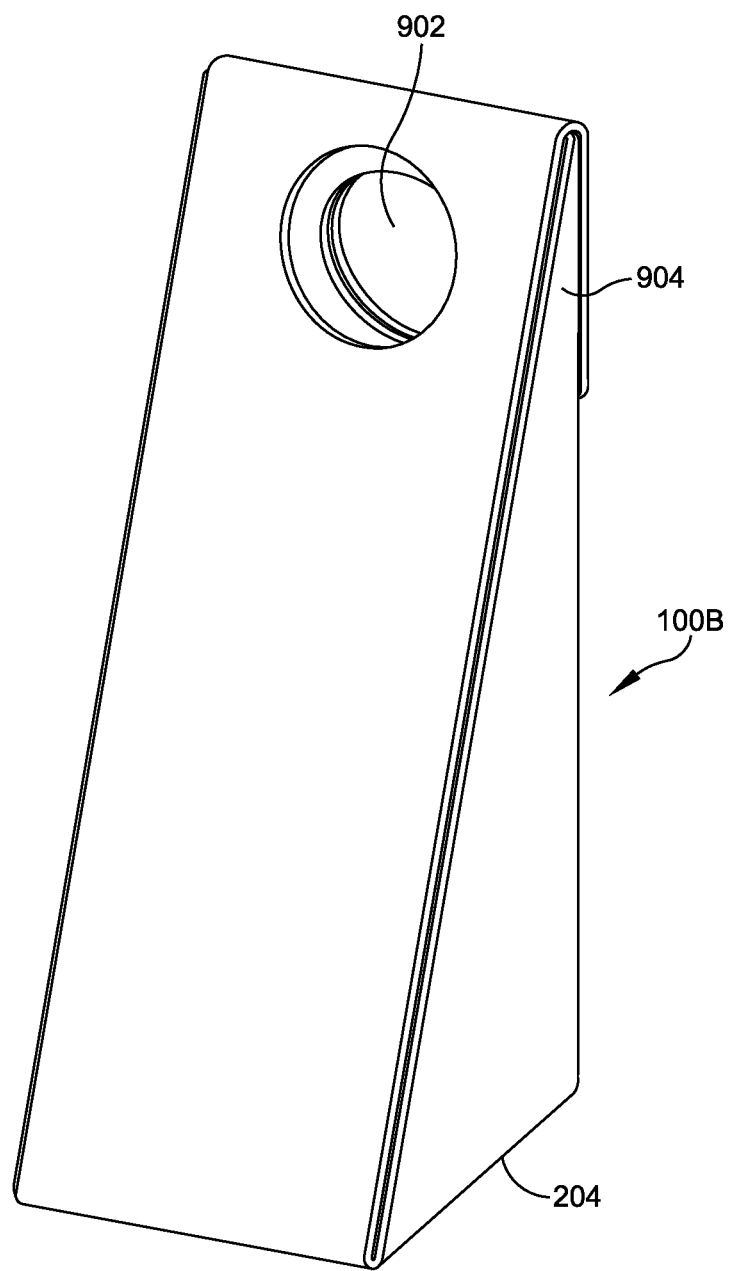
FIG. 9 is a perspective view of the kit package of FIG. 2 with its extended lip sealed around the upper end of the package in the orientation of FIG. 9, and showing the ornamental external configuration of the kit package.
Figure 10:
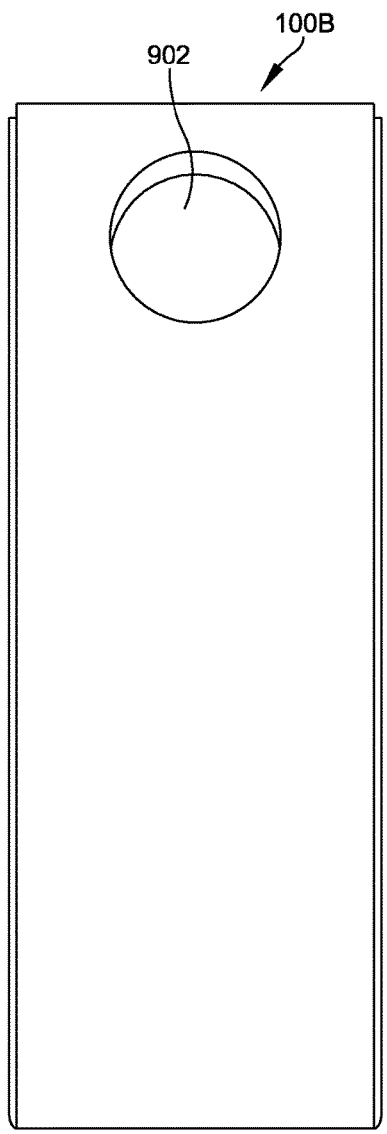
FIG. 10 is front elevational view of the kit package of FIG. 9.
Figure 11:
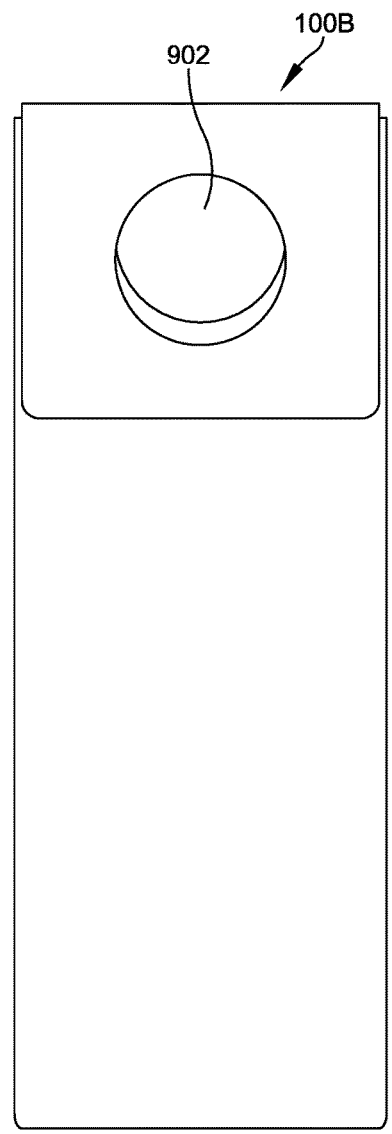
FIG. 11 is a rear elevational view of the kit package of FIG. 9.
Figure 12:
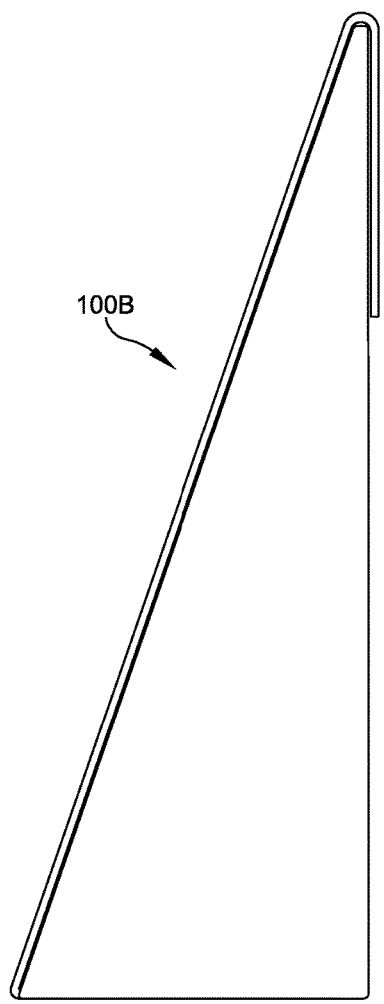
FIG. 12 is left side elevational view of the kit package of FIG. 9.
Figure 13:
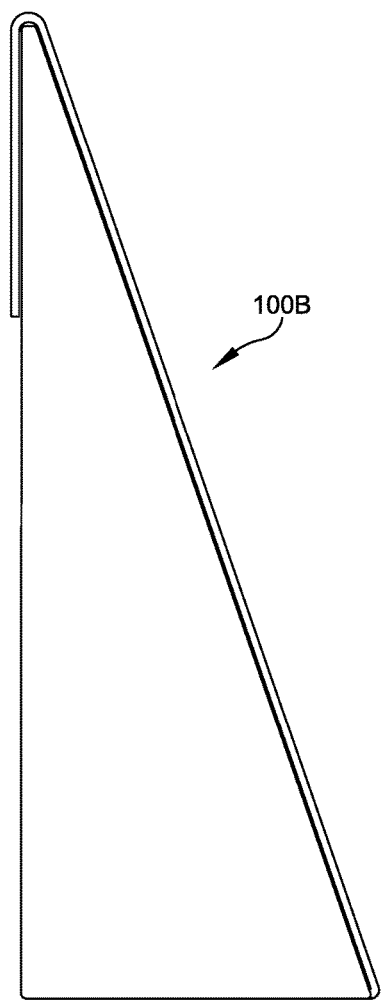
FIG. 13 is a right side elevational view of the kit package of FIG. 9.
Figure 14:
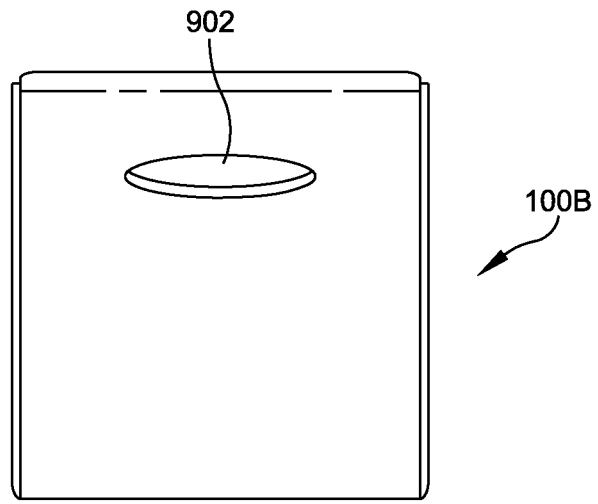
FIG. 14 is a top plan view of the kit package of FIG. 9.
Figure 15:
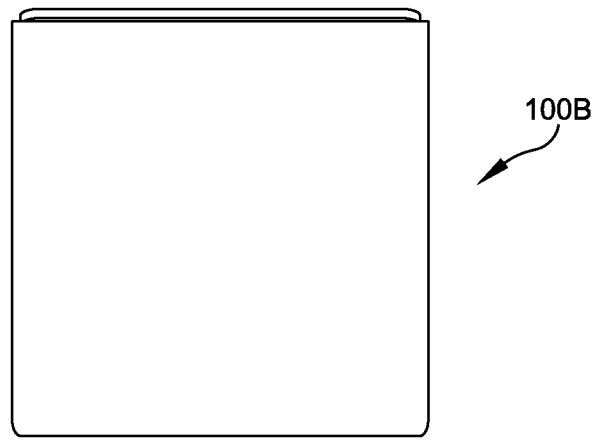
FIG. 15 is a bottom plan view of the kit package of FIG. 9.

With reference back to FIG. 2, when the kit package 100B of FIG. 2 is to be used by or for professional colorist for a client, the colorist can:
- prepare custom coloring formation for a client, commonly in connection with a hair coloring treatment provided by the colorist for the client; the formulation is made by mixing one or more differing colors and/or one or more differing enhancers and results in a relatively thick gel;
- open the kit package 100B as shown in FIG. 2 and either remove the inverted top compartment 220, bottom compartment 222, and mixing spatula 214 from the kit package 100B, or just remove the spatula from the kit package 100B and leave the top compartment 220 and bottom compartment 222 in position in the kit package 100B and in the following fill steps, fill the top 220 and bottom 222 compartments in that position (see also FIG. 8A);
- with reference to FIG. 8B, grasp the tabs of the top compartment interior seal 602 and remove the seal 602 from the top compartment 220, and use a spatula 802 to place the gel colorant 802 into the interior of the top compartment 220; in doing so, the colorist can use the top compartment linear markings, e.g., 621, to insert the proper quantity of coloring formulation to place within the top compartment 220 (0.5 ounce typically will be enough to treat at least the client's part line and front hairline regrowth after about two weeks; 1.5 ounce will typically be sufficient to treat all hair regrowth on the client);
- with reference to FIG. 8C, grasp the tabs of the bottom compartment interior seal 612 and remove the seal 612 from the bottom compartment 222, and pour peroxide 804 (typically between 0.5 to 1 ounce), which the colorist may have previously customized for the client as well, into the interior of the bottom compartment 222; in doing so, the colorist can use the bottom compartment linear markings, e.g., 618, to determine the proper quantity of peroxide to place within the top compartment 220;

with reference to FIG. 8D, grasp the tabs of the top compartment's interior seal 602 to slide the interior seal 602 to abut the gel colorant 802 within the interior of the top compartment 220;

with reference to FIG. 8E, grasp the tabs of the bottom compartment's interior seal to slide the interior seal 612 to abut the upper surface of the peroxide 804 within the interior of the bottom compartment 222;

with reference to FIG. 8G then invert the top compartment 220 and, grasping the top compartment 220 with one hand and the bottom compartment 220 with the other, push against the finger indent 306 to thread top compartment threads 806 into mating bottom compartment threads 808 and lock the top compartment 220 to the bottom compartment 222 by friction fit between the opposed threads 806, 808, yielding the sealed container 810 as shown in FIGS. 8G and 8H;

as shown in FIG. 8I, remove the removable component mounting platform insert 206 (as shown in FIG. 8A), place the applicator brush 214 and mixing spatula 218 back in the kit package 100B, place the mixing container 810 in the package with the longest peripheral side 811 of the container 810 abutting the widened end 204, close and re-seal the kit package 100B (as shown in FIG. 9), and give the package and the sealed container 810 to the client or to someone for the client; note that in this orientation of the container 810 in the closed package 100B, the container 810 is generally secured in position by the opposed applicator brush 214 and spatula 218 abutting opposed sides 813, 815 of the container 810, the widened end 204 of the package, and the matingly slanted underside 817 abutting the slanted end 819 of the container 810; and, if desired:

repeat the above process to the extent desired to provide the client with one or more addition additional sealed colorant and peroxide containers, re-sealed kit packages, or other kit components as desired. Since each such container will typically be for a single hair coloring retouching service, providing one or more additional such containers can allow the client to have one or more additional retouching service sessions.

Differing entities may perform differing steps, or portions of steps above. In some embodiments, for example, the main objective can be to have the steps performed so that a custom hair coloring formulation container is provided to the professional colorist's client for later use by or for the client. Thus, various parts of the method, and components, also may not be utilized if desired.

Further, the kit may include yet other or multiple components. For example, the colorist may provide the client with multiple mixing containers so that the client may utilize one container for one retouching session and another container for a second retouching session.

Figure 8J:
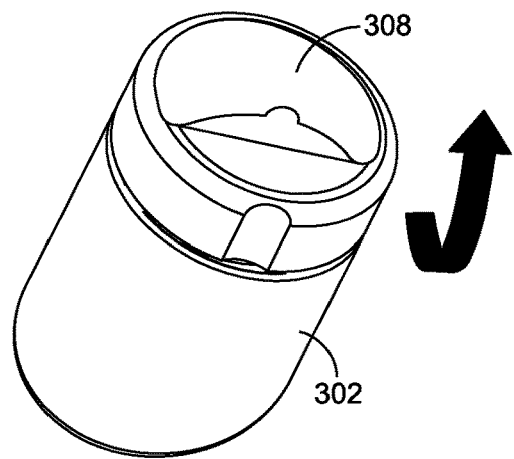
FIG. 8J is a perspective view of the assemble hair coloring container of FIG. 9G but with the top compartment's top side flexible seal being removed.
Figure 8K:
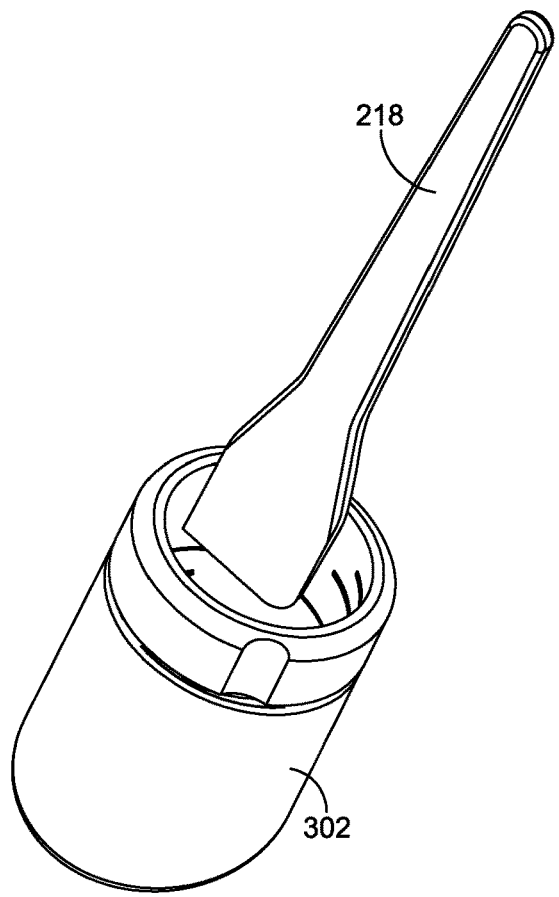
FIG. 8K is a perspective view of the hair coloring container of FIG. 8H but with the top compartment's top side seal removed and the kit's spatula penetrating the exposed channel in the top side of the top compartment.
Figure 8L:
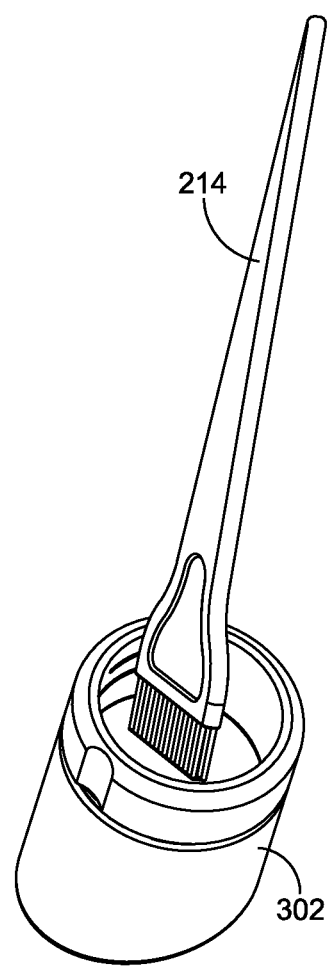
FIG. 8L is a perspective of the hair coloring container of FIG. 9K but with the kit's applicator brush penetrating the exposed channel to pick up mixed hair colorant with peroxide.

The client or other user may later implement the following method, such as, for example, when hair regrowth occurs on the client:

with reference to FIG. 8I, open the kit package 100B and remove the mixing container 810, applicator brush 214, mixing spatula 218, and instructions if in the kit package 100B;

read the instructions, which as noted supra can be on the underside 224 of the package;

with reference to FIG. 8F, unscrew the mixing container's top compartment 220 from the bottom compartment 222 and remove the interior seals 602 and 612 from the top 220 and bottom 222 compartments, respectively (making sure to maintain the bottom compartment in an upright position);

with reference to FIG. 8J, remove the top side seal 308 from the mixing container 302;

with reference to FIG. 8K, use the mixing spatula 218 to mix the hair colorant with the peroxide in the container;

with reference to FIG. 8L, use the applicator brush 214 to dip intro the mixed colorant-and-peroxide formulation to apply the mixture to regrowth hair; and at the appropriate time rinse the mixture from the hair.

Again, differing entities may perform differing steps, or portions of steps, above. In some embodiments, for example, the main objective can be to have the steps performed so that at least custom hair coloring formulation is provided to the professional colorist's client for later use by or for the client. Various parts of the method, and components, may not be utilized if desired.

In one embodiment, the sealing container 302 may weigh from 0.1 to 0.5 lb. depending on its compositing and size. The entire package kit 100B such as shown in FIG. 2 can weigh from 0.3 to 1 lbs. These container and kit can thus be very lightweight.

Further, all components of the particular kit 100B shown in FIG. 2 can be recyclable, and the kit 100B is easy to package, store, and ship. If desired, the client can return the mixing container to the professional colorist for refilling of the mixing container or reuse of the mixing container by or for the professional colorist and/or the client or another person or entity.

Referring now to FIGS. 9 through 16, this embodiment of the kit package 100B can be stood upright with its widened end 204 resting on a flat surface (not shown). Alternatively, the package kit may be mounted to a mounting rod or other similar structure (not shown) penetrating the circular mounting rod passage 902 penetrating the narrower upper section 904 of the package 100B. Mounting rod passage 902 can also be used to help carry the package 100B by inserting a finger through the passage 902.

The colorant mixing container and method may be different than as described above. For example, a wide variety of storage, injection, and mixing systems can be used to provide two compartments for the colorant and peroxide, respectively, and then mixing of the two. Exemplary such systems can include:

use of two syringe-like structures that can both suck in colorant and peroxide respectively and eject them into a mixing container of any type;

two-chamber syringe-like injectors, with mixing commenced at least by ejection of the colorant and peroxide through a single exit port; the chambers may be parallel to each other with each penetrated by a plunger, or the chambers may be laterally aligned and separated by a breakable seal, with one end of the two chamber structure penetrated by a plunger and the other end having and ejection port;

two-camber plastic bags with a common exit port opposite a sealable opening end (such as by ziplock), with the colorant and peroxide stored separately, such as in separate ziplock bags, until injected into the two chambers, respectively; a plurality of such bags can be pre-formed in strip of plastic or other suitable material and the rolled up to be delivered to a user, so the user can tear off one two chamber bag as needed;

a two chamber ampule (with one chamber abutting the other laterally along the lateral length of the ampule), with each chamber having an injection port for receipt of colorant and peroxide, respectively, with the colorant and peroxide injectable through the ports in a variety of ways, one of which can be by separate ampules containing the colorant and peroxide respectively;

simply having two separate containers (of any suitable type, such as without limitation, toothpaste tube-like tubes with an ejection end opposite an openable and re-sealable end, re-sealable boxes, bottles, plastic containers, etc.) to store the colorant and peroxide separately prior to use by mixing them in any suitable other container or mixing bowl; and/or a sealable box or oblong container, made of any suitable material, with a removable separator forming two laterally separated chambers in the container, one for colorant and one for peroxide.

With regard to application of colorant from the kit, the application tool could include: a sponge or other material for applying the colorant to hair; a plastic, rubber, metal, or silicon finger-tip cap with a resilient applicator material or brush on the external side of the cap, such as at the tip, side, or both; a blotter, or a bottle or container cap with an external applicator such as, for example, a brush, sponge, or blotter. In this regard, the kit can also include one or a pair of plastic or rubber gloves to prevent contact of the user's hand with the colorant and peroxide formulation.

With regard to the removable seals used in containers such as specified supra, the seals can have other features, such as a pin hole for passage of air through the seal. When placed in position adjacent colorant or peroxide in the container, a sealing adhesive or tape can be used to seal the hole, or in the case of a seal adjacent colorant, the colorant can penetrate the hole and seal it.

The seals may be secured in position in a container in differing ways, such as by mating channels in the interior wall of the container or by threads in the periphery of the seal for threading of the seal into mating threads in the container interior wall. Alternatively or in addition, the sealing structure can be provided by a plug structure with an O-ring surrounding the periphery of the plug. Further, a given seal (external or internal) may be puncturable so that, rather than removing a seal to accomplish mixing, the seal is left in place and punctured by a tool to allow colorant to then be mixed with peroxide in the container.

With regard to the top side seal or other seal covering a passage into a container structure, the sealing function can be accomplished in other ways. Other such structures can include plugs, caps securable to mating structure on the container, such as by mating threads, resilient lip structure, etc.

With regard to mixing of colorant with peroxide, yet other mixing techniques can be used, including breaking or removal of a seal or other chamber-separating structure and simply shaking the container or using a rotatable mixing device penetrating a passage in the container. Mixing tools also can include a non-stick or hydrophobic surface, so that colorant or a colorant component will be less likely to stick to that surface.

With regard to indicia for identifying the quantity of material placed into a chamber, container, etc., this indicia can be provided in the structures identified herein in any other suitable ways. The container, bag, chamber structure, etc., can be transparent or sufficiently translucent and have the indicia marked on the outside of structure.

The various alternative structures and methods described above may be mixed and matched as desired. Features may also be deleted as desired. Generally speaking, however, one objective of the method is to prevent colorant from oxidizing excessively prior to its use to color hair or otherwise be utilized to accomplish coloration.

Additional Considerations:

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100B % in either direction and thus provide support for claims that recite such values or any and all ranges or subranges that can be formed by such values. For example, a stated numerical value of 8 should be understood to vary from 0 to 16 (100B % in either direction) and provide support for claims that recite the range itself (e.g., 0 to 16), any subrange within the range (e.g., 2 to 12.5) or any individual value within that range (e.g., 15.2).

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean,"

etc.). References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The subject matter recited in the claims is not coextensive with and should not be interpreted to be coextensive with any embodiment, feature, or combination of features described or illustrated in this document. This is true even if only a single embodiment of the feature or combination of features is illustrated and described in this document.

What is claimed is:

1. A custom hair coloring kit comprising in combination:
a peroxide container section having a bottom wall, a side wall and a top end opposite the bottom wall, where the peroxide container is configured to contain a hydrogen peroxide developer composition;
a hair colorant container section including a first interior sidewall intermediate a top end and opposed bottom end in the hair colorant container section;
a first removable and reusable colorant seal removably and reusably mountable to the first interior sidewall within the hair colorant container section mountable spaced from a second removable colorant seal mounted to the top end of hair colorant container section where the second removable colorant seal forms a removable external sealing surface of the hair colorant container section, where the hair colorant container is configured to contain a hair colorant composition between the first and second colorant seals and within a hollow interior defined by the sidewall;
a mixing tool; and
a hair coloring kit package comprising:
two opposed, parallel, planar triangular sides, each triangular side having a widened end and a narrow, pointed end opposite the widened end;
two opposed planar rectangular sides, each rectangular side extending from the widened end of the opposed triangular sides to the pointed end of the triangular sides;
the triangular sides and rectangular sides forming an interior having a triangular prism shape;
a mounting platform mounted within the interior, the mounting platform extending from the widened end to the narrow end, the mounting platform having a first opening surrounding the hair colorant container section and a second opening surrounding the peroxide container section, the first opening or second opening being closer to the widened end than the narrowed end; and
wherein the hair colorant container section and peroxide container section are removable from the openings in the mounting platform and mountable together to form a unitary container in which the peroxide container forms a bottom portion of the unitary container, the first sealing surface is located adjacent the top end of the peroxide container and the second external sealing surface forms a distal, top end of the unitary container.

2. The custom hair coloring kit of claim 1 further comprising a removable and reusable peroxide seal removably and reusably mountable within the peroxide container section.

3. The custom hair coloring kit of claim 1 wherein the hair colorant container section is threadably mountable to the peroxide container section.

4. The custom hair coloring kit of claim 2 wherein the hair colorant container section is threadably mountable to the peroxide container section.

5. The custom hair coloring kit of claim 4 wherein the hair coloring kit package has a kit mounting bar passage penetrating transversely the two opposed planar rectangular sides at the narrower section of the customer coloring kit package.

6. The hair coloring kit of claim 1, wherein the mixing tool is a mixing spatula, and the kit further comprising an applicator brush adjacent an interior side of one of the triangular sides, where the mixing spatula is adjacent an interior of the opposing triangular side.

7. The hair coloring kit of claim 6, wherein the hair colorant container section is threadably mountable to the peroxide container section.

8. The hair coloring kit of claim 1, further including a kit mounting bar passage transversely penetrating the narrower section of the customer hair coloring kit package.

9. The hair coloring kit of claim 7, further including a kit mounting bar passage transversely penetrating the narrower section of the customer hair coloring kit package.

10. The hair coloring kit of claim 1 wherein the side wall of the peroxide container section has a tubular outer periphery defining a longer side and an opposing shorter side, where the bottom wall extends at an acute angle from the longer side to the opposing shorter side.

11. The hair coloring kit of claim 9 wherein the side wall of the peroxide container section has a tubular outer periphery defining a longer side and an opposing shorter side, where the bottom wall extends at an acute angle from the longer side to the opposing shorter side.

* * * * *